United States Patent [19]

Bernhard et al.

[11] Patent Number: 4,883,887

[45] Date of Patent: Nov. 28, 1989

[54] SULFONE POLYENE INTERMEDIATES

[75] Inventors: Kurt Bernhard, Lupsingen; Stephan Jäggli, Bubendorf; Paul Kreienbühl, Riehen; Ulrich Schwieter, Reinach, all of Switzerland

[73] Assignee: Hoffmann-La Roche Inc., Nutley, N.J.

[21] Appl. No.: 214,567

[22] Filed: Jul. 1, 1988

[30] Foreign Application Priority Data

Jul. 9, 1987 [CH] Switzerland .......... 2615/87
May 9, 1988 [CH] Switzerland .......... 1749/88

[51] Int. Cl.$^4$ .......... C07D 317/72; C07C 147/08
[52] U.S. Cl. .......... 549/341; 549/342; 549/369; 549/370; 549/375; 549/415; 549/420; 549/421; 560/11; 560/194; 562/429; 568/28; 568/31; 568/32; 568/33; 568/34
[58] Field of Search .......... 568/28, 31, 32, 33, 568/34; 562/429; 560/194, 11; 549/370, 375, 369, 341, 342, 415, 420, 421

[56] References Cited

U.S. PATENT DOCUMENTS

| | | | |
|---|---|---|---|
| 3,960,967 | 6/1976 | Olson et al. | 564/440 |
| 4,147,708 | 4/1979 | Manchand | 260/413 |
| 4,331,814 | 5/1982 | Chabardes et al. | 560/225 |

FOREIGN PATENT DOCUMENTS 2224606 9/1972 Fed. Rep. of Germany .
2305267 8/1973 Fed. Rep. of Germany .
2708210 9/1977 Fed. Rep. of Germany .

OTHER PUBLICATIONS

Julia et al, Tetrahedron Letters, vol. 23, No. 24, p. 2465 (1982).
Bremmer et al, Tetrahedron Letters, vol. 23, No. 24, p. 3265 (1982).
Julia et al, Tetrahedron, vol. 42, No. 9, pp. 2469, 2475 (1986).
Otera, Chemistry Letters, p. 1883 (1985).
Field, J. Am. Chem. Soc., vol. 74, p. 3919 (1952).
Fischli, Helv. Chim. Acta, vol. 58, Fasc 5 Nr 161-162 p. 1492 (1975).
Manchand, Helv. Chim. Acta, vol. 59 Fasc 2 Nr 43-44, p. 387 (1976).
Manchand, J. Org. Chem. vol. 43, No. 25, 4769 (1978).
Mandai, J. Am. Chem. Soc. 1984, 106, p. 3670.

*Primary Examiner*—Mary E. Ceperley
*Attorney, Agent, or Firm*—Jon S. Saxe; George M. Gould; William H. Epstein

[57] ABSTRACT

A process for producing carotenoids and carotenoid intermediates via reduction of sulfonyl polyenes with a dithionite in the presence of ammonia or an aliphatic amine, including novel intermediates in this process, which carotenoids are known coloring agents for foodstuffs, animal feeds, pharmaceuticals, etc.

22 Claims, No Drawings

SULFONE POLYENE INTERMEDIATES

BACKGROUND OF THE INVENTION

It is fundamentally known that sulfones can form β-hydroxysulfones with aldehydes and ketones and that the sulfonyl group can be eliminated in a reductive manner after the dehydration of the β-hydroxysulfone to the vinylsulfone. The known reduction methods are, however, generally suitable only for simply molecules and are often not stereospecific. For example, the reduction with sodium dithionite and sodium hydrogen carbonate is for the most part not suitable or only poorly suitable for polyenes. On the other hand, the β-hydroxysulfones are not very stable and in the case of the present polyene systems can not be prepared, since evidently reversible decomposition occurs.

The hitherto known applications of sulfones to the manufacture of carotenoids have therefore been concerned with reactions with halides, esters etc to give sulfones which have the sulfonyl group on a saturated C—C bond and from which the sulfonyl group can be eliminated by reaction with base.

SUMMARY OF THE INVENTION

The present invention is directed to a process for the manufacture of the compounds of the formula

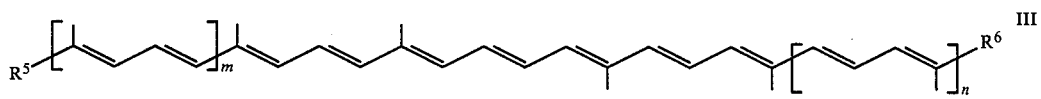

wherein m and n are independently 0 or 1; $R^5$ and $R^6$ are independently selected from the group consisting of formyl, 4-methyl-3-pentenyl, formyl protected with an acetal protecting group, carboxy, carboxy esterified with an ester protecting group and a group of the formula:

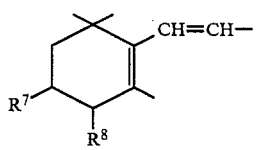

$R^7$ and $R^8$ are each independently selected from the group consisting of hydrogen, hydroxy, hydroxy protected with a protecting group, oxo or oxo protected with a protecting group, with the proviso that when m is 1, $R^5$ is 4-methyl-3-pentenyl; and when m is 0, $R^5$ is other than 4-methyl-3-pentenyl; and when n is 1, $R^6$ is 4-methyl-3-pentenyl; and when n is 0, $R^6$ is other than 4-methyl-3-pentenyl;

which process comprises reducing a compound of the general formula

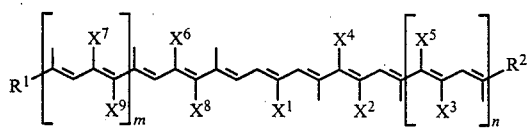

wherein m and n are as above; $R^1$ and $R^2$ are selected from the group consisting of 4-methyl-3-pentenyl, formyl protected with an acetal protecting group, carboxy, carboxy esterified with an ester protecting group, and a group of the formula:

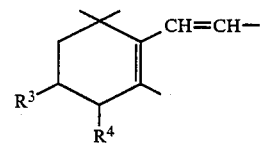

$R^3$ and $R^4$ are hydrogen, hydroxy, hydroxy protected with a protecting group, oxo or oxo protected a protecting group; with the proviso that when m is 1, $R^1$ is 4-methyl-3-pentenyl; and when m is 0, $R^1$ is other than 4-methyl-3-pentenyl; and when n is 1, $R^2$ is 4-methyl-3-pentenyl and when n is 0, $R^2$ is other than 4-methyl-3-pentenyl; only one of $X^1$, $X^2$, $X^3$, $X^4$ and $X^5$ being a sulfonyl residue while the others are hydrogen; and $X^6$, $X^7$, $X^8$ and $X^9$ all being hydrogen except in the case where $R^1$ and $R^2$ are both selected from the same group and $X^1$ is hydrogen, then in this case, $X^6$ can be either hydrogen or a sulfonyl residue if $X^2$ is a sulfonyl residue; $X^7$ can be either hydrogen or a sulfonyl residue if $X^3$ is a sulfonyl residue, $X^8$ can be either hydrogen or a sulfonyl residue, if $X^4$ is a sulfonyl residue, and $X^9$ can be either hydrogen or a sulfonyl residue if $X^5$ is a sulfonyl residue with dithionite in an aqueous-organic solvent mixture in the presence of ammonia or an aliphatic amine and, if desired, cleaving off protecting groups present.

Compounds of formula III are either known carotenoids where the protecting groups have been cleaved off or known intermediates for carotenoids. Carotenoids are known coloring agents for foodstuffs, perfumes pharmaceuticals and animal feeds.

In producing compounds of formula III from compounds of formula I where $R^1$ and $R^2$ is acetalized formyl and/or $R^3$ and/or $R^4$ is a protected oxo, the corresponding compound of formula I where $R^5$ and/or $R^6$ is an acetalized formyl and/or $R^7$ and/or $R^8$ is a protected oxo is produced. In order to produce the compound of formula I where $R^5$ and/or $R^6$ are formyl and/or $R^7$ and/or $R^8$ are oxo, the compound of formula I produced by the dithionite reduction is subjected to cleavage to remove the acetal or other protecting groups.

DETAILED DESCRIPTION

In protecting the formyl group, any conventional group which will form a protective acetal can be utilized. The term "acetalized formyl group" embraces in the scope of the present invention conventional acetalized aldehyde groups, especially groups of the formula —CH(OR$^{13}$)$_2$ in which each of the residues $R^{13}$ signifies $C_1$–$C_5$-alkyl or both residues together signify $C_2$–$C_6$-alkylene, such as dimethoxymethyl or 1,3-dioxolan-2-yl.

The term "esterified carboxy group" embraces any conventional ester protecting group which can be utilized to protect the organic carboxylic acid group. Any of such groups can be utilized in accordance with esterified carboxy residues, especially ($C_1$–$C_5$-alkoxy)carbonyl such as methoxycarbonyl, ethoxycarbonyl and the like.

The term "protected hydroxy group" embraces conventional protected hydroxy groups, especially acyloxy groups and etherified hydroxy groups. Any conventional hydroxy protecting groups which can be cleaved to reform the hydroxy group can be utilized in accordance with this invention.

The term "acyloxy group" embraces conventional carboxylic acid ester residues, especially alkanoyloxy with from 1 to 8 carbon atoms such as formyloxy, acetoxy or propionyloxy as well as aroyloxy such as benzoyloxy.

The term "etherified hydroxy group" embraces usual ether protecting groups, especially $C_1$-$C_5$-alkoxy such as methoxy or ethoxy, and groups of the formula $-O-CR^{14}R^{15}-OR^{16}$ in which $R^{14}$ and $R^{15}$ signify hydrogen or $C_1$-$C_5$-alkyl and $R^{16}$ signifies $C_1$-$C_5$-alkyl or $R^{15}$ and $R^{16}$ together also signify $C_2$-$C_6$-alkylene, such as 1-methoxy-1-methylethoxy or tetrahydropyranyloxy.

In accordance with this invention the oxo group can be protected with any of the conventional aldehyde or ketone protecting groups which can be cleaved to regenerate the oxo group. As used herein the term "protected oxo group" embraces usual protected oxo groups. The acetalized oxo groups are prefered, especially those in which the term protected oxo group stands for two $C_1$-$C_5$-alkoxy groups (e.g. for 2 methoxy groups) or for a $C_2$-$C_6$-alkylenedioxy group (e.g. ethylenedioxy or 2,3-butylenedioxy). Further, an oxo group can also be protected as the enol ether. This method is primarily preferred in the case of α-hydroxyketones, in which case the etherification of the enediol can be effected preferably also by dimerization or by the formation of a cyclic acetal (e.g. with acetone to give the acetonide).

The term "sulfonyl residue" designates any conventional sulfonyl residues used in Julia reactions. Preferably, the term stands for substituted or unsubstituted phenysulfonyl, especially for residues of the formula $-SO_2-R^{17}$ in which $R^{17}$ signifies unsubstituted phenyl or phenyl substituted with halogen, phenyl, phenoxy, $C_1$-$C_5$-alkyl and/or $C_1$-$C_5$-alkoxy such as phenylsulfonyl, p-chlorophenylsulfonyl, 4-biphenylylsulfonyl, p-phenoxyphenylsulfonyl, p-tolylsulfonyl, p-methoxyphenylsulfonyl and the like.

The term "halogen" includes all halogens particularly fluorine, chlorine, bromine and iodine.

The term "alkyl" embraces straight-chain and branched groups having preferably 1-5 carbon atoms such as methyl, ethyl, propyl, isopropyl, t-butyl and the like. The term "alkoxy" embraces alkyloxy groups in which "alkyl" has the given significance. The term "alkylene" embraces straight-chain and branched, divalent aliphatic saturated hydrocarbons with preferably 2-6 carbon atoms, e.g. 2,3-butylene or especially polymethylene such ethylene, trimethylene, tetramethylene, pentamethylene, hexamethylene and the like.

The term "aliphatic amine" embraces in the scope of the present invention amines and hydroxylamines in which the carbon atom directly linked with the amino group is saturated or the carbon atoms directly linked with the amino group are saturated. The term also embraces amines having 2 or more amino groups.

The term "alkali metal" embraces lithium, sodium and potassium and the term "alkaline earth metal" embraces magnesium, calcium, strontium and barium.

The polyenes of formula I and III as well as the others disclosed herein embrace in each case all cis/trans and E/Z isomers or mixtures thereof unless expressly indicated to the contrary. In general, the all-E isomers are preferred. In the case of double bonds which have a sulfonyl residue, the E-form correponds to the cis-configuration (with respect to the carbon residues), in the remaining cases the E-form corresponds to the trans-configuration.

The reaction in accordance with the invention with dithionite in the presence of ammonia or an aliphatic amine surprisingly enables the compounds of formula III to be produced in high yield starting from the sulfonylpolyenes of formula I. Moreover, the reduction proceeds in high stereoselectivity. For example, starting from all-E-sulfones of formula I there are obtained predominantly the all-trans compounds of formula III. The sulfones of formula I are crystalline compounds and are therefore easy to purify, which additionally facilitates the manufacture of isomer-pure compounds of formula III.

The reduction of the compounds of formula I can be effected with usual dithionites, for example with sodium dithionite, zinc dithionite, barium dithionite, tetraalkylammonium dithionite (e.g. methyl-tridecylammonium dithionite) and the like. An alkali metal dithionite, especially sodium dithionite, is preferably used. The dithionite is conveniently used in at least about equimolar amounts, preferably in an amount of about 1-5 mol equivalents or more based on the sulfone of formula I.

The reduction of the compounds of formula I is effected in the presence of ammonia or an aliphatic amine. The amines preferably have a pKa value (measured in aqueous solution at 20° C.) of at least about 9 and particularly of at least about 9.25 (pKa value of ammonia). This is fulfilled by practically all compounds which are usually referred to as aliphatic amines. Examples of preferred aliphatic amines are the alkylamines such as methylamine, ethylamine, n-butylamine or t-butylamine, the dialkylamines such as dimethylamine or diethylamine, the trialkylamines such as trimethylamine or triethylamine, the cyclic amines such as pyrrolidine, piperidine or quinuclidine, the alkylenediamines such as ethylenediamine, putrescine or hexamethylenediamine, the aralkylamines such as benzylamine or phenylethylamine, the hydroxylamines such as N-ethylhydroxylamine, N,N-dimethylhydroxylamine or N-benzyl-N-methyl-hydroxylamine, and the like. Here, "aralkyl" preferably signifies phenylalkyl. Especially preferred nitrogen bases are ammonia, the alkylamines, the dialkylamines, the trialkylamines, the cyclic aliphatic amines and the alkylenediamines. The amount of ammonia or amine is not critical; as a rule, however, a significant excess, for example about 5-30 mol equivalents based on the sulfone of formula I, is preferably used.

The reduction is conveniently carried out in an aqueous-organic solvent mixture. Suitable organic components of the solvent mixture are inert organic solvents, for example ethers such as diethyl ether, diisopropyl ether, tetrahydrofuran, dioxan or 1,2-dimethoxyethane, saturated or aromatic hydrocarbons such as hexane, cyclohexane, benzene or toluene, amides such as dimethylformamide and the like. The ethers, especially tetrahydrofuran and 1,2-dimethoxyethane, are preferred organic solvents. Temperature and pressure are not critical. For example, the reduction in accordance with the invention can be carried out at atmospheric pressure and a temperature of about 0° C. to the reflux temperature, preferably at about room temperature to 50° C.

If desired, protecting groups which may be present in the product obtained can be cleaved off according to known methods, for example by hydrolysis with acid or base.

In carrying out the reduction of the compound of formula I, with a dithionite reducing agent, all oxo and/or formyl groups should be protected during this reaction. This reaction produces the compound of formula III with the oxo and/or formyl groups protected. These protecting groups can be removed after the dithionite reduction by conventional means.

In the reduction in accordance with the invention a cis-double bond at the sulfone group (E-form) is converted almost exclusively into a trans-double bond, and vice versa, while the configuration of the remaining double bonds is preserved. If desired, the product can be isomerized according to known methods, for example by heating in water or an organic solvent, in order to increase the amount of all-trans isomer. The purification of the product of formula I can be effected in a known manner, for example in a chromatographic manner and/or by recrystallization.

nyl residue and $X^1$, $X^2$, $X^3$, $X^5$, $X^6$, $X^7$ and $X^9$ signify hydrogen. When $X^6$ or $X^8$ denotes a sulfonyl residue, n has the significance of m and $R^2$ has the significance of $R^1$. When $X^6$ and $X^8$ denote hydrogen, $R^2$ preferably stands for an acetalized formyl group or for an optionally esterified carboxy group.

A further group of preferred compounds of formula I comprises those in which m and n are 1, $R^1$ and $R^2$ are 4-methyl-3-pentenyl, either the two groups $X^3$ and $X^7$ or the two groups $X^5$ and $X^9$ represent sulfonyl residues and the remainder of the groups $X^1$–$X^9$ are each signify hydrogen.

A further group of preferred compounds of formula I comprises those in which $X^1$ is a sulfonyl residue and $X^2$–$X^9$ is hydrogen.

Formula I above embraces all cis/trans isomers as well as mixtures thereof. Depending on the choice of isomer or isomer mixture there can be obtained different isomers or isomer mixtures of the compounds of formula III. In general, there are especially preferred the all-E-sulfones of formula I which lead directly to the important all-trans isomers of formula III.

The all-E forms of preferred groups of compounds of formula I are the following:

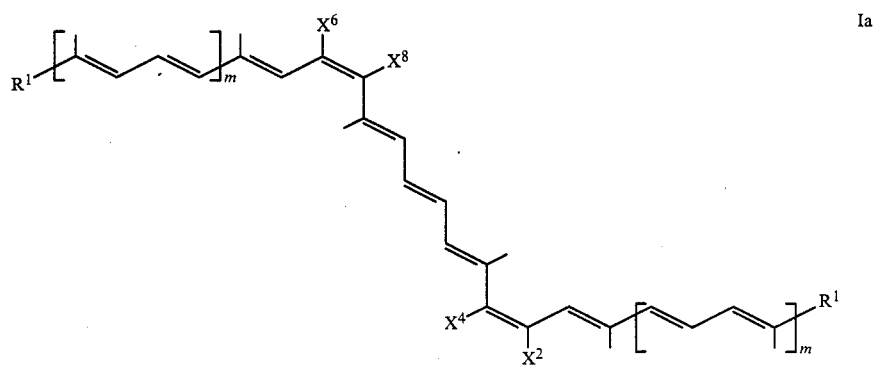

The compounds of formula I are novel and are likewise an object of the present invention.

A preferred group of compounds of formula I comprises those in which either $R^2$ signifies a sulfonyl residue, $X^6$ signifies hydrogen or a sulfonyl residue and $X^1$, $X^3$, $X^4$, $X^5$, $X^7$, $X^8$ and $X^9$ signify hydrogen or $X^4$ signifies a sulfonyl residue, $X^8$ signifies hydrogen or a sulfowherein $X^2$ and $X^6$ are sulfonyl residues and $X^4$ and $X^8$ are hydrogen or $X^2$ and $X^6$ are hydrogen and $X^4$ and $X^8$ are sulfonyl residues and m and $R^1$ are as above;

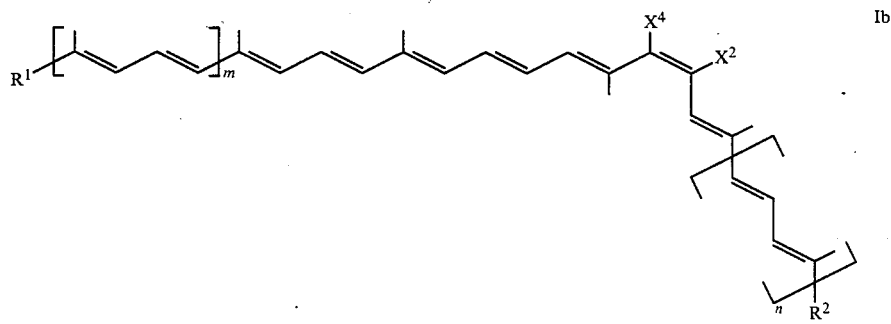

wherein $X^2$ is a sulfonyl residue and $X^4$ is hydrogen or $X^2$ is hydrogen and $X^4$ is a sulfonyl residue and m, n, $R^1$ and $R^2$ are as above;

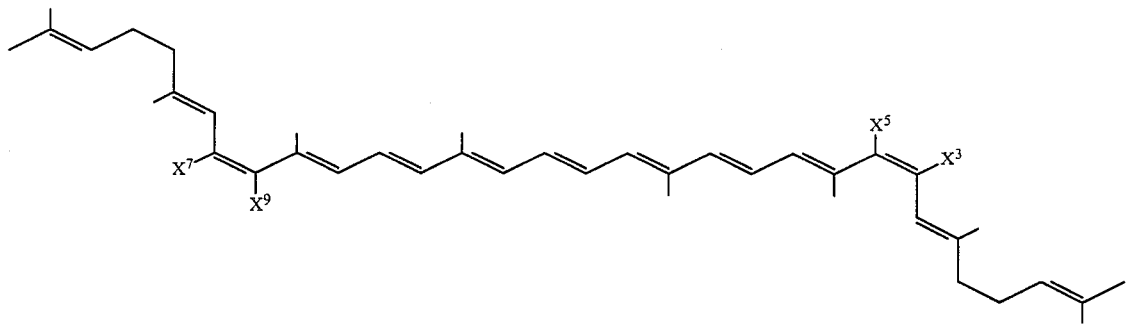

Ic wherein $X^3$ and $X^7$ are sulfonyl residues and $X^5$ and $X^9$ are hydrogen or $X^3$ and $X^7$ are hydrogen and $X^5$ and $X^9$ are sulfonyl residues;

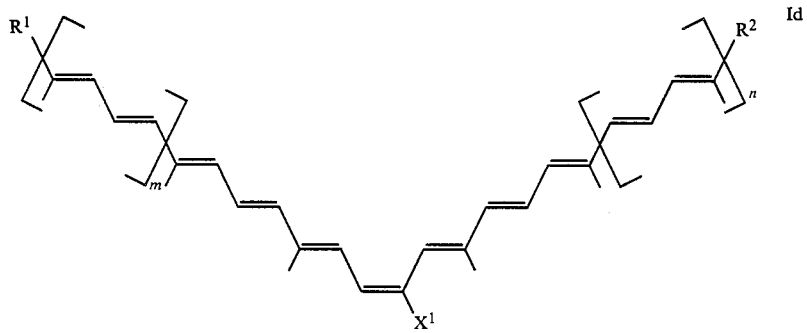

Id wherein $X^1$ is a sulfonyl residue and m, n, $R^1$ and $R^2$ are as above.

In general, there are preferred those compounds of formulae I, Ib and Id in which $R^1$ and $R^2$ are selected from the same group or $R^2$ is an acetalized formyl group. Further, there are preferred those compounds of formulae I, Ia, Ib and Ic in which $X^1$, $X^2$ or $X^3$ is a sulfonyl residue.

In formula II above $R^3$ preferably is hydrogen or an optionally protected hydroxy group, especially hydrogen, hydroxy, acetoxy, methoxy or 1-methoxy-1-methylethoxy. $R^4$ preferably is hydrogen or a protected oxo group, especially hydrogen, ethylenedioxy or two methoxy groups.

The compounds of formula I can be prepared in accordance with the invention by (a) reacting a compound of the general formula

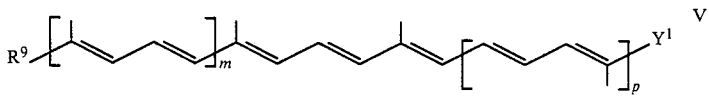

V with a compound of the general formula

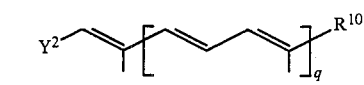

VI or (b) reacting a compound of the general formula

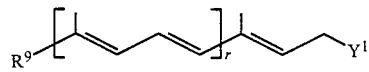

VII with a compound of the general formula

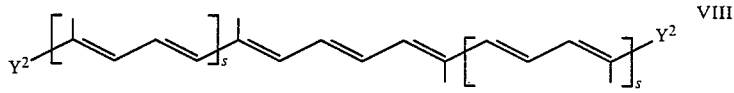

VIII wherein m and n are 0 or 1; $R^9$ and $R^{10}$ are individually selected from the group consisting of acetalized formyl, carboxy, carboxy esterified with an ester protecting group or a group of the formula:

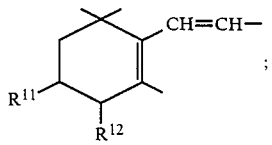

IX and 4-methyl-3-pentenyl; $R^{11}$ and $R^{12}$ are individually selected from the group consisting of hydrogen, hydroxy, hydroxy protected with a protecting group, and oxo protected with a protecting group, one of $Y^1$ and $Y^2$ being individually formyl whereas the other being $-CH_2X$ with X being a sulfonyl residue; p and q being 0, 1 or 2 with the limitation that the sum of p and q is equal to n+1; r and s individually being 0 or 1 with the sum of r and s being equal to m; and with the proviso that when m is 1, $R^9$ is 4-methyl-3-pentenyl and when m is 0, $R^9$ is other than 4-methyl-3-pentenyl; and with the further proviso that when n is 1, $R^{10}$ is 4-methyl-3-pentenyl and when n is 0, $R^{10}$ is other than 4-methyl-3-pentenyl,
in an inert organic solvent in the presence of a base and, after the addition of an acylating agent, converting the resulting compound of the general formula

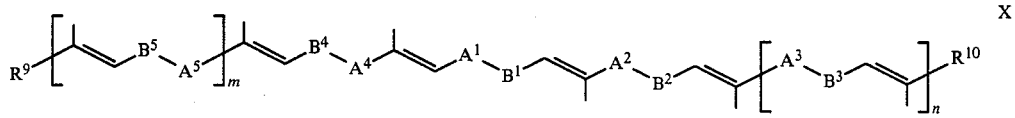

wherein X, $R^9$, $R^{10}$, $R^{11}$, $R^{12}$, m and n are as above; one of $-A^1-B^1-$, $-A^2-B^2-$ and $-A^3-B^3-$ is $-CHX-CH(OR)-$ or $-CH(OR)-CHX-$ while the others are $-CH=CH-$; $-OR$ is acyloxy; $-A^4-B^4-$ and $-A^5-B^5-$ are both $-CH=CH-$ except in the case where $R^9$ and $R^{10}$ are both selected from the same group and m is equal to n, then in this case $-A^4-B^4-$ can be either $-CH=CH-$ or $-CHX-CH(OR)-$ if $A^2-B^2$ is $-CHX-CH(OR)-$; or $-A^4-B^4-$ can be either $-CH=CH-$ or $-CH(OR)-CHX-$ if $A^2-B^2$ is $-CH(OR)-CHX-$; $-A^5-B^5-$ can be $-CH=CH-$ or $-CHX-CH(OR)-$ if $-A^3-B^3-$ is $-CHX-CH(OR)-$; or $A^5-B^5-$ can be $-CH=CH-$ or $-CH(OR)-CHX-$ if $-A^3-B^3-$ is $-CH(OR)-CHX-$,
into a compound of formula I with aqueous base.

The reaction of a compound of formula V with a compound of formula VI and the reaction of a compound of formula VII with a compound of formula VIII can be effected in a manner known per se in an inert organic solvent. As deprotonizing agents there can be used usual bases, for example alkyl derivatives of alkali metals, Grignard reagents, alkali metal amides, alkali metal hydrides and the like, such as methyllithium, butyllithium, ethylmagnesium bromide, diethylmagnesium, lithium diisopropylamide and sodium hydride. Examples of suitable solvents are the ethers such as diethyl ether, diisopropyl ether, t-butyl methyl ether, tetrahydrofuran, dioxan and 1,2-dimethoxyethane, the saturated and aromatic hydrocarbons such as hexane, cyclohexane, benzene and toluene, and the like. Temperature and pressure are not critical. However, in general, the reaction is carried out at atmospheric pressure and a temperature of about −80° C. to room temperature, preferably at a temperature of about −70° C. to about −15° C.

As a rule, no β-hydroxysulfones can be isolated from the reaction mixture. It is therefore important that an acylating agent is added to the reaction mixture without previous working-up. It has been found that the β-acyloxysulfones of formula X can be prepared in good yield and, if desired, can be isolated from the reaction mixture. Moreover, the compounds of formula X can be converted readily into compounds of formula I.

The reaction to the acyloxy derivative of formula X can be effected with usual acylating agents, for example with acyl anhydrides, acyl chlorides or acyl bromides. Here, the term "acyl" preferably has the same significance as in the acyloxy groups referred to earlier. The preparation of the acetoxy derivatives of formula X with acetic anhydride is especially preferred. The acylating agent is preferably used in excess. Temperature and pressure are not critical. However, in general, the acylation is carried out at atmospheric pressure and a temperature of about −70° C. to room temperature, preferably at about −20° C. to about +10° C. Free hydroxy groups which may be present in $R^9$ and/or $R^{10}$ are likewise acylated in this reaction.

The convertion of a compound of formula X into a compound of formula I can be effected conveniently with aqueous base. The conversion is preferably carried out with an alkali metal hydroxide or alkaline earth metal hydroxide in water. Sodium hydroxide solution or potassium hydroxide solution is especially preferred. If desired, an inert organic solvent can be added to the reaction mixture. Examples of suitable organic solvents are the solvents mentioned above in connection with the preparation of the compounds of formulx X, especially the ethers. Temperature and pressure are not critical. However, in general, the reaction is carried out at atmospheric pressure and a temperature of about 0° C. to the reflux temperature, preferably at about 0° C. to room temperature. Ester groups which may be present in $R^9$ and/or $R^{10}$ can be preserved or saponified in the reaction with aqueous base depending on the base which is used, the concentration of base, the reaction temperature, the reaction time and the like.

The preparation of the compounds of formula I can preferably also be carried out as a one-pot process without isolation of the compounds of formula X. In accordance with this variant the aqueous base can be added directly to the reaction mixture after completion of the acylation.

The configuration of the double bonds in the compounds of formulae V-VIII is largely preserved in the conversion to compounds of formulae X and I. The double bonds in formula I which are substituted with a sulfonyl residue are generally formed predominantly in the E-form. Starting from the trans isomers or the all-trans isomers of the compounds of formulae V and VI or the compounds of formulae VII and VIII there can therefore be obtained directly predominantly the preferred all-trans isomers of the compounds of formula X and the preferred all-E isomers of the compounds of formula I.

The compounds of formula X are novel and are likewise an object of the present invention. Formula X embraces the compounds of the formula

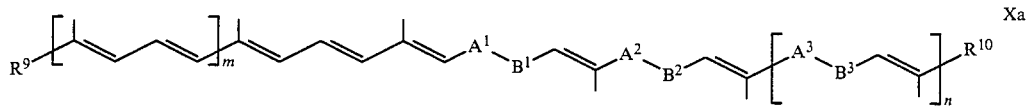

wherein $R^9$, $R^{10}$, m, n, $-A^1-B^1-$, $-A^2-B^2-$ and $-A^3-B^3-$ are as above,
which are obtainable by reacting a compound of formula V with a compound of formula VI, and the compounds of the general formula

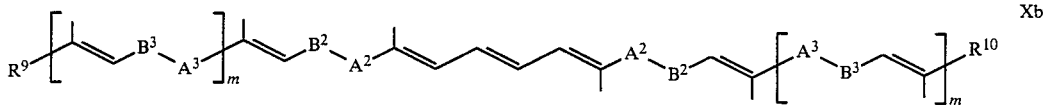

wherein $-A^2-B^2-$ is $-CHX-CH(OR)-$ or $-CH(OR)-CHX-$ and $-A^3-B^3-$ is $-CH=CH-$ or $-A^2-B^2-$ is $-CH=CH-$ and $-A^3-B^3-$ is $-CHX-CH(OR)-$ or $-CH(OR)-CHX-$; and $R^9$, m, X and R are as above,
which are obtainable by reacting a compound of formula VII with a compound of formula VIII.

Preferred compounds of formulae X, Xa and Xb are those which lead to preferred compounds of formula I. There are preferred, for example, the all-trans isomers as well as those compounds in which one of the groups $-A^1-B^1-$, $-A^2-B^2-$ and $-A^3-B^3-$ is $-CHX-CH(OR)-$. Preferred sulfonyl residues X, acyloxy groups $-OR$ and protecting groups are the groups referred to earlier.

The compounds of formulae V–VIII which are used as starting materials are known compounds and can be prepared readily according to methods known per se.

The invention is illustrated in more detail by the following Examples.

EXAMPLE 1

(a) 90.9 g (240 mmol) of 5-(2,6,6-trimethyl-1-cyclohexenyl)-3-methyl-2E,4E-pentadienyl (p-chlorophenyl)-sulfone were dissolved in 500 ml of tetrahydrofuran in a round flask having a mechanical stirrer, dropping funnel, thermometer and argon gasification and the solution was cooled to −70° C. (ethanol/dry ice bath). There were subsequently added dropwise to the reaction solution within 15 minutes 150 ml of a 1.6M solution of butyllithium (240 mmol) in hexane and then within 20 minutes a solution of 16.4 g (100 mmol) of (all-E)-2,7-dimethyl-2,4,6-octatrienedial in 800 ml of tetrahydrofuran. The mixture was stirred at −60° C. for a further 3 hours and then treated dropwise within 10 minutes with 136 ml (1.4 mol) of acetic anhydride, whereby the temperature rose distinctly. The reaction mixture containing (all-E)-12,12'-diacetoxy-11,11'-bis[(p-chlorophenyl)sulfonyl]-11,12,11',12'-tetrahydro-β,β-carotene was stirred for a further 2 hours at 0°–5° (ice bath), thereafter treated within 20 minutes with 600 ml of 28 percent aqueous sodium hydroxide solution (5.5 mol) and stirred overnight without cooling. The reaction mixture was subsequently poured on to ice-water and extracted with methylene chloride. The organic phase was washed neutral with 5 percent potassium dihydrogen phosphate solution and with water and concentrated to an amount of about 1 kg on a rotary evaporator. Solvent and water were distilled off from the orange suspension obtained and diisopropyl ether was simultaneously added dropwise until a boiling of 66° C. had been reached (solvent exchange). The suspension (about 500 ml) was stored overnight in a refrigerator and then suction filtered. The crystals were dried at 45° C. in a water-jet vacuum. There were thus obtained 74.5 g (84%) of (all-E)-β,β-caroten-11,11'-ylene bis[(p-chlorophenyl)sulfone] as orange crystals with m.p. 172°–173° C. and a content of all-E isomer of 94%. The oil (36 g) which was obtained by evaporation of the mother liquor and which contained 35% product in accordance with chromatographic analysis was not worked-up.

(b) 3.54 g (4 mmol) of (all-E)-β,β-caroten-11,11'-ylene bis[(p-chlorophenyl)sulfone] were dissolved in 354 ml of 1,2-dimethoxyethane in a sulphonation flask having a mechanical stirrer, thermometer and argon gasification. This solution was treated firstly with 7.5 ml of 25 percent aqueous ammonia (100 mmol) and then while cooling (ice bath) with a solution of 7.0 g of 85 percent sodium dithionite (34 mmol) in 100 ml of water. The internal temperature thereby rose to 30° C. The mixture was stirred at 25°–30° C. for a further 5 hours and then poured on to 200 ml of water and 250 ml of methylene chloride in a separating funnel. The organic phase was washed with 200 ml of 5 percent aqueous potassium dihydrogen phosphate solution and twice with 100 ml of water each time, dried over sodium sulphate, filtered and evaporated. There were thus obtained 2.17 g of crude β-carotene as a violet glistening solid residue. The crude product was dissolved in methylene chloride and then treated dropwise with methanol with the simultaneous removal of the methylene chloride by distillation. The resulting suspension in methanol was boiled at reflux for a further 1 hour and then cooled to 0° C. Filtration and drying of the residue in a high vacuum gave 1.92 g (90%) of black-violet crystalline β-carotene with m.p. 170°–174° C. which contained 90% of all-E isomer and 3% of 9Z isomer. The oil (0.26 g) obtained by concentration of the mother liquor was not worked-up.

In an analogous experiment, the reaction mixture containing (all-E)-12,12'-diacetoxy-11,11'-bis[(p-chlorophenyl)sulfonyl]-11,12,11',12'-tetrahydro-β,β-carotene was worked-up by extraction with phosphate buffer solution (pH 7), water and t-butyl methyl ether. The organic phases were dried over sodium sulphate, filtered and concentrated. Recrystallization of the resulting white crystalline powder from methylene chloride and diethyl ether gave (all-E)-12,12'-diacetoxy-11,11'-bis[(p-chlorophenyl)sulfonyl]-11,12,11',12'-tetrahydro-β,β-carotene with m.p. 178°–179° C. (decomposition from 160° C.).

EXAMPLE 2

(a) 22.4 g (65 mmol) of 5-(2,6,6-trimethyl-1-cyclohexenyl)-3-methyl-2E,4E-pentadienyl phenylsulfone were dissolved in 125 ml of tetrahydrofuran in a round flask having a mechanical stirrer, dropping funnel, thermometer and argon gasification and the solution was cooled to −70° C. (ethanol/dry ice bath). There were subsequently added dropwise to the reaction mixture within 15 minutes 40.6 ml of a 1.6M solution of butyllithium (65 mmol) in hexane and then within 20 minutes a solution of 4.1 g (25 mmol) of (all-E)-2,7-dimethyl-2,4,6-octatrienedial in 200 ml of tetrahydrofuran. The mixture was stirred at −60° C. for a further 3 hours and then treated dropwise within 10 minutes with 37.4 ml (0.4 mol) of acetic anhydride, whereby the temperature rose distinctly. The reaction mixture containing (all-E)-12,12'-diacetoxy-11,11'-bis(phenylsulfonyl)-11,12,11',12'-tetrahydro-$\beta,\beta$-carotene was stirred for a further 2 hours at 0°–5° C. (ice bath), thereafter treated rapidly at −5° C. with 165 ml of 28 percent aqueous sodium hydroxide solution (1.52 mol) and stirred overnight without cooling. The reaction mixture was subsequently extracted with 5 percent aqueous potassium dihydrogen phosphate solution and a mixture of diethyl ether and methylene chloride (vol. 5:3). The organic phase was dried over sodium sulphate, filtered and concentrated. The crude product obtained was dissolved in 200 ml of methylene chloride. The solution was concentrated to an amount of 100 g on a rotary evaporator, then treated with 100 ml of diisopropyl ether and again concentrated to 100 g, whereby product began to separate out. This suspension was again treated with 100 ml of diisopropyl ether, then concentrated to 100 g and stored at 4° C. for 3 hours for the completion of crystallization. Filtration and drying of the crystals in a high vacuum gave 14.3 g (70%) of (all-E)-$\beta,\beta$-caroten-11,11'-ylene bis(phenylsulfone) as an orange powder with m.p. 190°–191° C., which contained 92% of all-E isomer and 8% of other isomers. The oil (13.2 g) which was obtained by concentration of the mother liquor and which contained further product as an isomer mixture was not worked-up.

(b) The (all-E)-$\beta,\beta$-caroten-11,11'-ylene bis (phenylsulfone) obtained was converted into $\beta$-carotene in an analogous manner to Example 1b.

EXAMPLE 3

(a) 890 mg (2 mmol) of (all-E)-9-(2,6,6-trimethyl-1-cyclohexenyl)-3,7-dimethyl-2,4,6,8-nonatetraenyl (p-chloro-phenyl)sulfone [retinyl (p-chlorophenyl)sulfone] were dissolved in 3 ml of tetrahydrofuran under an inert gas in a multi-necked flask having a magnetic stirrer and thermometer. The solution was cooled to −70° C. and subsequently treated dropwise firstly within 15 minutes with 1.25 ml of a 1.6M solution of butyllithium (2 mmol) in hexane and then within 15 minutes with a solution of 284.4 mg (1 mmol) of vitamin A aldehyde (retinal) in 4 ml of tetrahydrofuran. The reaction mixture was stirred at −70° C. for a further 4 hours and then treated with 0.756 ml (8 mmol) of acetic anhydride. The mixture was stirred at 0° C. for a further 2 hours and then at room temperature overnight. Thereafter, the reaction mixture containing (all-E)-15'-acetoxy-15-(p-chlorophenyl)sulfonyl-15,15'-dihydro-$\beta,\beta$-carotene was treated rapidly at 0°–5° C. with 3.5 ml of 28 percent aqueous sodium hydroxide solution (32 mmol) while cooling well and stirred at room temperature for a further 6.5 hours. Thereafter, the reaction mixture was extracted with water and with 5 percent potassium dihydrogen phosphate solution. The wash solutions were back-extracted with methylene chloride. The combined organic phases were dried over sodium sulphate, filtered and concentrated on a rotary evaporator. There were thus obtained 1.1 g of (all-E)-$\beta,\beta$-caroten-15-yl (p-chlorophenyl)sulfone which was used in the next step without further purification.

(b) The resulting (all-E)-$\beta,\beta$-caroten-15-yl (p-chlorophenyl)sulfone (1.1 g) was dissolved in 12.5 ml of tetrahydrofuran. This solution was treated with 1.3 ml (12.5 mmol) of diethylamine and with a solution of 0.875 g of 85 percent sodium dithionite (4.27 mmol) in 12.5 ml of water and stirred at room temperature for a further 7.5 hours. Thereafter, the reaction mixture was extracted with 5 percent aqueous potassium dihydrogen phosphate solution and with 2 percent aqueous sodium chloride solution. The wash solutions were back-extracted with methylene chloride. The organic phases were combined and concentrated. The red oil obtained was taken up in 100 ml of water and heated to reflux for 21 hours. Thereafter, the mixture was suction filtered, whereby 850 mg of crude product remained behind as a dark red powder. This crude product was digested in 160 ml of cyclohexane and the insoluble residue was filtered off under suction. The filtrate was separated by chromatography on silica gel with cyclohexane/toluene (vol. 9:1). Concentration of the product-containing fractions and drying in a high vacuum gave 280 mg of $\beta$-carotene with m.p. 170°–171° C. and a content of all-E isomer of 90%.

EXAMPLE 4

(a) 2.5 g (6 mmol) of (all-E)-9-(2,6,6-trimethyl-1-cyclohexenyl)-3,7-dimethyl-2,4,6,8-nonatetraenyl phenyl-sulfone [retinyl phenylsulfone] were dissolved in 9 ml of tetrahydrofuran under an inert gas in a multi-necked flask having a magnetic stirrer and thermometer. The solution was cooled to −$\alpha$° C. and subsequently treated dropwise firstly within 10 minutes with 3.72 ml of a 1.6M solution of butyllithium (6 mmol) in hexane and then within 10 minutes with a solution of 853 mg (3 mmol) of vitamin A aldehyde (retinal) in 12 ml of tetrahydrofuran. The reaction mixture was stirred at −60° C. for a further 70 minutes and then treated with 2.27 ml (24 mmol) of acetic anhydride. The mixture was stirred at 0° C. for a further 1.5 hours. Thereafter, the reaction mixture containing (all-E)-15'-acetoxy-15-phenylsulfonyl-15,15'-dihydro-$\beta,\beta$-carotene was treated rapidly while cooling well at 0°–5° C. with 10.5 ml of 28 percent aqueous sodium hydroxide solution (96 mmol) and stirred at room temperature for a further 16 hours. Thereafter, the reaction mixture was extracted with water and with 5 percent potassium dihydrogen phosphate solution. The wash solutions were back-extracted with diethyl ether. The combined organic phases were dried over sodium sulphate, filtered and concentrated on a rotary evaporator. There were thus obtained 3.07 g of crude product as a red oil. Chromatographic separation on silica gel with hexane/acetone (vol. 1:1) gave 1.41 g of (all-E)-$\beta,\beta$-caroten-15-yl phenylsulfone.

(b) 338.5 g (0.5 mmol) of (all-E)-$\beta,\beta$-caroten-15-yl phenylsulfone were dissolved in 6.25 ml of tetrahydrofuran. This solution was treated with 0.65 ml (6.25 mmol) of diethylamine and with a solution of 0.44 g of 85 percent sodium dithionite (2.14 mmol) in 6.25 ml of water and stirred at room temperature for a further 3 days. Thereafter, the reaction mixture was extracted with tetrahydrofuran/diethyl ether. The organic phases were washed with 5 percent potassium dihydrogen phosphate solution and with 1 percent sodium chloride solution, dried over sodium sulphate, filtered and concentrated. The obtained crude product (255 mg) was treated with 2.5 ml of methylene chloride and 20 ml of hexane. This suspension was suction filtered and the residue was washed with hexane and dried in a high vacuum. There were thus obtained 176 mg of β-carotene as a dark red crystalline powder with m.p. 180°–181° C. and a content of all-E isomer of 94%.

EXAMPLE 5

(a) A solution of 2.5 g (8 mmol) of 3,7-dimethyl-2E,6E-octadienyl (p-chlorophenyl)sulfone in 16 ml of tetrahydrofuran was treated dropwise at −70° C. firstly within 10 minutes with 5 ml of a 1.6M solution of butyllithium (8 mmol) in hexane and then within 30 minutes with a solution of 593 mg (2 mmol) of crocetin dialdehyde [(all-E)-2,6,11,15-tetramethyl-2,4,6,8,10,12,14-hexadecaheptaenedial] in 100 ml of tetrahydrofuran. The suspension was stirred at −70° C. for a further 21 hours, then treated with 3 ml (31.7 mmol) of acetic anhydride and stirred at 0° C. for a further 8 hours. Thereafter, the red reaction mixture containing (all-E)-8,8'-diacetoxy-7,7'-bis[(p-chlorophenyl)sulfonyl]-7,8,7',8'-tetrahydrolycopene was treated while stirring well at 0°–10°C. with 13 ml of 28 percent aqueous sodium hydroxide solution (120 mmol) and stirred at room temperature for a further 40 hours. For the working-up, the reaction mixture was diluted with tetrahydrofuran and water. The organic phase was separated and washed with 50 ml of 5 percent potassium dihydrogen phosphate solution and with 50 ml of 2 percent sodium chloride solution. The wash solutions were back-extracted twice with 30 ml of hexane/methylene chloride (vol. 2:1) each time. The organic phases were concentrated without drying. The crude (all-E)-lycopen-7,7'-ylene bis[(p-chlorophenyl)-sulfone] obtained was used in the next step without further purification.

By chromatographic separation of a crude product, obtained in an analogous manner, on silica gel with cyclohexane/methylene chloride/diethyl ether (vol. 4:1:1) and recrystallization there was obtained pure (all-E)-lycopen-7,7'-ylene bis[(p-chlorophenyl)sulfone: m.p. 179°–180° C.

(b) The crude (all-E)-lycopen-7,7'-ylene bis[(p-chlorophenyl)sulfone obtained was taken up in 177 ml of tetrahydrofuran. The solution was treated at −5° C. to +5° C. with 5.2 ml (50 mmol) of diethylamine and with a solution of 3.5 g of 85 percent sodium dithionite (17 mmol) in 50 ml of water and stirred at room temperature for a further 3 days. Thereafter, the reaction mixture was extracted with 5 percent aqueous potassium dihydrogen phosphate solution and with 2 percent aqueous sodium chloride solution. The wash solutions were back-extracted with ethyl acetate. The organic phases were combined and concentrated. The crude product obtained was taken up in 200 ml of water and heated to reflux for 10 hours. The mixture was subsequently cooled and suction filtered. The residue was washed with water and recrystallized from a mixture of methylene chloride and methanol. There were thus obtained 884 mg of lycopene (psi,psi-carotene) as violet platelets which contained 92.8% of all-trans isomer and 4% of 5-cis isomer. By suspension in methylene chloride, filtration and drying there was obtained lycopene with m.p. 165°–166° C. and a content of all-trans isomer of 98%.

EXAMPLE 6

(a) A solution of 6.1 g (20 mmol) of 1-[4(R)-(1-methoxy-1-methylethoxy)-2,6,6-trimethyl-1-cyclohexenyl]-3-methyl-1E,4-pentadien-3-ol in 20 ml of hexane was treated dropwise at −5° C. to 0° C. while stirring with a solution of 6.6 ml (40 mmol) of sodium benzenesulphinate in 30 ml of acetic acid/water (vol. 80:20). The mixture was stirred at −5° C. to 0° C. for a further 23 hours and then at 50° C. for 3 hours. The cooled reaction mixture was subsequently poured into 50 ml of ethyl acetate and 100 ml of water. The aqueous phase was separated and back-extracted four times with 25 ml of ethyl acetate each time. The organic phases were washed three times with 100 ml of 2 percent sodium chloride solution each time, twice with 50 ml of semi-saturated sodium hydrogen carbonate solution each time and once more with 50 ml of 2 percent sodium chloride solution, then dried over sodium sulphate, filtered and concentrated. Drying of the oil obtained in a high vacuum at 35° C. gave 6.67 g (92.5%) of 5-[4(R)-hydroxy-2,6,6-trimethyl-1-cyclohexenyl]-3-methyl-2E,4E-pentadienyl phenylsulfone as a yellow-brown resin.

(b) A solution of 6.67 g (18.5 mmol) of 5-[4(R)-hydroxy-2,6,6-trimethyl-1-cyclohexenyl]-3-methyl-2E,4E-pentadienyl phenylsulfone in 37 ml of tetrahydrofuran was placed in a sulphonation flask while gassing with argon. The solution was cooled to −60° C. and treated dropwise while stirring firstly within 20 minutes with 23.3 ml of a 1.6M solution of butyllithium (37.3 mmol) in hexane and then within 15 minutes with a solution of 759 mg (4.6 mmol) of (all-E)-2,7-dimethyl-2,4,6-octatrienedial in 37 ml of tetrahydrofuran. The reaction mixture was stirred at −70° C. for a further 4 hours, then treated with 16.6 ml (176 mmol) of acetic anhydride and stirred at −5° C. over-night. Subsequently, the yellow reaction mixture containing (all-E)-3(R),12,3'(R),12'-tetraacetoxy-11,11'-bis-(phenylsulfonyl)-11,12,11',12'-tetrahydro-zeaxanthin was treated while stirring well at 0°–10° C. with 98 ml (900 mmol) of 28 percent aqueous sodium hydroxide solution and stirred further at room temperature. For the working-up, the reaction mixture was extracted with 250 ml of methylene chloride and with 250 ml of water. The organic phase was separated and washed with 125 ml of 5 percent potassium dihydrogen phosphate solution and with 125 ml of water. The aqueous phases were back-extracted with methylene chloride. The organic phases were combined, dried over sodium sulphate, filtered and concentrated. There were thus-obtained 9.2 g of crude product as a red oil which, in addition to educt, consisted mainly of (all-E)-R,R'-zeaxanthin-11,11'-ylene bis-(phenylsulfone) and its monoacetate and its diacetate in the ratio of about 1:2:7.

(c) The crude product obtained (9.2 g) was dissolved in 800 ml of 1,2-dimethoxyethane and 24.5 ml (236 mmol) of diethylamine while gassing with argon. This solution was treated at about 25° C. with a solution of 16.1 g of 85 percent sodium dithionite (78.6 mmol) in 230 ml of water. The reaction mixture was stirred at 25°–30° C. for a further 45 minutes and then poured into 400 ml of ice-water and 500 ml of methylene chloride. The organic phase was separated and washed with 400 ml of 5 percent potassium dihydrogen phosphate solution and twice with 200 ml of water each time. The aqueous phases were back-extracted twice with 200 ml of methylene chloride each time. The organic phases were combined, dried over sodium sulphate, filtered and concentrated. There were thus obtained 7.6 g of a semi-crystalline crude product which contained (all-E)-R,R'-zeaxanthin and its monoacetate and its diacetate in the ratio of about 1:2:7.

(d) A solution of the crude product obtained (7.6 g) in 77 ml of methanol was treated with 1.5 g (1.1 mmol) of solid potassium carbonate and stirred at room temperature overnight. The mixture was subsequently suction filtered (rinsing with a small amount of methanol) and the filtrate (mother liquor I) was saved. The filter cake consisting of potassium carbonate and zeaxanthin was dissolved in water and methylene chloride. The organic phase was separated, dried over sodium sulphate, filtered and concentrated. Drying of the resulting powder overnight in a high vacuum at room temperature gave 500 mg of (all-E)-R,R'-zeaxanthin. Mother liquor I was concentrated, then treated with 60 ml of methanol and heated to reflux for 24 hours. Thereafter, the mixture was cooled to 0° C. and suction filtered (rinsing with a small amount of methanol). The filter cake was dried for 16 hours in a high vacuum at room temperature, there being obtained a further 136 mg of (all-E)-R,R'-zeaxanthin. Total yield of isolated zeaxanthin: 636 mg of crystalline (all-E)-R,R'-zeaxanthin with m.p. 191°–193° C. The filtrate (mother liquor II) was concentrated and digested with 20 ml of methylene chloride. The insoluble residue was filtered off under suction. Concentration of the filtrate gave 3.1 g of red oil which was not worked-up.

EXAMPLE 7

(a) A solution of 24.6 g of 5-[4(R)-acetoxy-2,6,6-trimethyl-1-cyclohexenyl]-3-methyl-2E,4E-pentadienyl acetate (purity about 88%) in 150 ml of 2-propanol was treated at 50° C. with a suspension of 100 g of 62 percent sodium p-chlorobenzenesulphinate in 200 ml of water and the mixture was stirred at 80° C. for 24 hours. For the working-up, the reaction mixture was poured at room temperature into a mixture of 80 ml of methylene chloride and 320 ml of hexane. The organic phase was separated and washed three times with 200 ml of water each time. The aqueous phases were back-extracted with 200 ml of methylene chloride/hexane (vol. 1:4). The organic phases were combined, dried over sodium sulphate, filtered and concentrated. There were thus obtained 27.4 g of crude product as an orange-brown oil which was separated by chromatography on silica gel with hexane/tert.butyl methyl ether. The pure fractions were concentrated on a rotary evaporator up to the beginning of crystallization, then left to crystallize out in a refrigerator and suction filtered (rinsing with cold hexane). The filter cake was dried for 16 hours in a high vacuum at room temperature, there being obtained 13.4 g of 5-[4(R)-acetoxy-2,6,6-trimethyl-1-cyclohexenyl]-3-methyl-2E,4E-pentadienyl (p-chlorophenyl)sulfone as a white powder with m.p. 101°–102° C. Concentration of the mother liquor gave a further 3.8 g of product with about 10% cis content as a semi-crystalline mass.

(b) 5-[4(R)-Acetoxy-2,6,6-trimethyl-1-cyclohexenyl]-3-methyl-2E,4E-pentadienyl (p-chlorophenyl)sulfone was converted into (all-E)-R,R'-zeaxanthin in an analogous manner to Example 6, steps b-d, via (all-E)-3(R),12,3'-(R),12'-tetraacetoxy-11,11'-bis[(p-chlorophenyl)sulfonyl]-11,12,11',12'-tetrahydro-zeaxanthin and the diacetate of (all-E)-R,R'-zeaxanthin-11,11'-ylene bis-[(p-chlorophenyl)sulfone.

EXAMPLE 8

(a) 34 ml (400 mmol) of 36 percent hydrochloric acid were treated dropwise while stirring and gassing with nitrogen at 25°–30° C. within 15 minutes with a solution of 24 g (100 mmol) of 3-(3-hydroxy-3-methyl-1E,4-pentadienyl)-2,4,4-trimethyl-2-cyclohexen-1-one (purity 97.6%) in 100 ml of methylene chloride. The mixture was stirred at 25°–30° C. for a further 20 minutes and then poured into 100 ml of saturated sodium chloride solution. The organic phase was separated and washed with 100 ml of saturated sodium chloride solution and with 100 ml of semi-saturated sodium hydrogen carbonate solution. The aqueous phase was back-extracted twice with 100 ml of methylene chloride each time. The organic phases were combined, dried over sodium sulphate and a small amount of potassium carbonate, filtered and concentrated to a volume of about 40 ml. After the addition of 100 ml of dimethylformamide the remaining methylene chloride was distilled off from the mixture.

(b) The resulting solution of 3-(5-chloro-3-methyl-1E,3E-pentadienyl)-2,4,4-trimethyl-2-cyclohexen-1-one in dimethylformamide was diluted with 100 ml of dimethylformamide and then treated at 10° C. with 24.8 g (125 mmol) of sodium p-chlorobenzenesulphinate. The reaction mixture was stirred at 70° C. for 1 hour and then poured into 2 l of water and treated with 350 ml of methylene chloride. The organic phase was separated and washed twice with 1 l of semi-saturated sodium hydrogen carbonate solution each time and once with 1 l of water. The aqueous phases were back-extracted with 250 ml of methylene chloride. The organic phases were dried over sodium sulphate, filtered and concentrated. The beige powder obtained (39 g) was dissolved in methylene chloride and recrystallized by adding diisopropyl ether and distilling off the methylene chloride. The crystals were filtered off and dried for 16 hours in a water-jet vacuum at 40° C. Yield: 22.6 g of 5-(2,6,6-trimethyl-3-oxo-1-cyclohexenyl)-3-methyl-2E,4E-pentadienyl (p-chlorophenyl)sulfone.

(c) A mixture of 1.2 g (3 mmol) of 5-(2,6,6-trimethyl-3-oxo-1-cyclohexenyl)-3-methyl-2E,4E-pentadienyl (p-chlorophenyl)sulfone, 2 ml (12 mmol) of triethyl orthoformate, 0.67 ml (12 mmol) of ethylene glycol and 3 mg of p-toluenesulphonic acid was stirred at 30° C. for 2 hours. Thereafter, the mixture was treated with 2 ml (12 mmol) of triethyl orthoformate, 0.67 ml (12 mmol) of ethylene glycol and 3 mg of p-toluenesulphonic acid and stirred for a further 2 hours. The reaction mixture was subsequently treated with 30 mg of sodium hydrogen carbonate and extracted with diethyl ether/methylene chloride. The organic phase was washed with semi-saturated sodium chloride solution and with water. The wash solutions were back-extracted with diethyl ether. The organic phases were dried over sodium sulphate, filtered and concentrated. The yellow oil obtained (2.26 g) was crystallized from pentane. The crystals were filtered off under suction and dried for 16 hours in a high vacuum at 40° C. Yield: 1.13 g of 5-(6,8,8-trimethyl-1,4-dioxaspiro[4,5]dec-6-en-7-yl)-3-methyl-2E,4E-pentadienyl (p-chlorophenyl)sulfone as a white powder with m.p. 126°–128° C.

(d) A solution of 1.05 g (2.4 mmol) of 5-(6,8,8-trimethyl-1,4-dioxaspiro[4,5]dec-6-en-7-yl)-3-methyl-2E,4E-penta-dienyl (p-chlorophenyl)sulfone in 8 ml of tetrahydrofuran was treated dropwise at −60° C. while gassing with nitrogen firstly within 10 minutes with 1.5 ml of a 1.6M solution of butyllithium (2.4 mmol) in hexane and then within 10 minutes with a solution of 164 mg (1 mmol) of (all-E)-2,7-dimethyl-2,4,6-octatrienedial in 8 ml of tetrahydrofuran. The mixture was stirred at −60° C. for a further 3.5 hours, then treated with 1.4 ml of acetic anhydride and stirred at 0° C. for 2 hours. Subsequently, the mixture containing (all-E)-12,12′-diacetoxy-4,4,4′,4′-bis(ethyl-enedioxy)-11,11′-bis[(p-chlorophenyl)sulfonyl]-11,12,11′,12′-tetrahydro-canthaxanthin was treated at −5° C. to +5° C. with 6 ml of 28 percent aqueous sodium hydroxide solution and stirred in an ice bath for 1 hour and at room temperature for 16 hours. Thereafter, the orange reaction mixture was extracted with methylene chloride. The organic phase was washed with saturated sodium carbonate solution and with 1 percent sodium chloride solution, dried over sodium sulphate, filtered and concentrated. The orange powder obtained (1.3 g) was recrystallized from methylene chloride/diisopropyl ether. Yield: 692 mg of (all-E)-4,4,4′,4′-bis(ethylenedioxy)-canthaxanthin-11,11′-ylene bis[(p-chlorophenyl)sulfone] as an orange powder.

(e) A suspension of 600 mg (0.6 mmol) of (all-E)-4,4,4′,4′-bis(ethylenedioxy)-canthaxanthin-11,11′-ylene bis[(p-chlorophenyl)sulfone in 60 ml of 1,2-dimethoxyethane was treated with 1.56 ml (15 mmol) of diethylamine and with a solution of 1.05 g of 85 percent sodium dithionite (5.1 mmol) in 15 ml of water. The mixture was stirred at 25°–30° C. for 3 hours, then poured into 50 ml of ice-water and treated with diethyl ether and methylene chloride. The aqueous phase was separated and back-extracted twice with 50 ml of diethyl ether/methylene chloride each time. The organic phases were washed twice with 50 ml of 5 percent potassium dihydrogen phosphate solution each time and then treated with 50 ml of water, 100 mg of p-toluenesulphonic acid and 5 ml of glacial acetic acid. The mixture was stirred at 30°–35° C. for 17 hours. Subsequently, the organic phase was separated, washed five times with 50 ml of 2 percent sodium hydrogen carbonate solution each time, dried over sodium sulphate, filtered and evaporated on a rotary evaporator. The dark violet powder obtained (341 mg of crude product) was treated with methylene chloride and methanol. After distilling off the methylene chloride the mixture was boiled under weak reflux for a further 4.5 hours and then cooled to 0°–5° C. The crystals were filtered off under suction and dried for 16 hours in a high vacuum at 40° C. Yield: 231 mg of (all-E)-canthaxanthin as a fine powder with m.p. 206°–208° C.

EXAMPLE 9

(a) A mixture of 146 g of 2-hydroxy-2-methyl-3-butenal dimethyl acetal, 175 ml of methylene chloride, 4.4 g of copper (II) chloride dihydrate and 225 ml of concentrated hydrochloric acid was heated to reflux for 20 hours while stirring. Subsequently, the reaction mixture was rinsed with 25 ml of methylene chloride into a stirring vessel. The organic phase was separated and the aqueous phase was extracted four times with 50 ml of methylene chloride each time. The organic phases were washed with 25 ml of 10 percent sodium chloride solution and with 25 ml of saturated sodium hydrogen carbonate solution, dried over sodium sulphate, filtered and evaporated. The crude product obtained was rinsed with a small amount of methylene chloride into a flask having a Hickmann headpiece. Subsequently, firstly the methylene chloride was distilled off in a water-jet vacuum at about 60° C. and then the product was flat distilled at 45°–55° C./2 Torr. There were thus obtained 99 g of γ-chlorotiglic aldehyde.

(b) 67 g of γ-chlorotiglic aldehyde were dissolved in 1 l of dimethylformamide while gassing with nitrogen. The solution was cooled to 10° C. and treated with 260 g of 62 percent sodium p-chlorobenzenesulphinate. The mixture was stirred at 70° C. for 1 hour, then poured on to ice/water and extracted with methylene chloride. The organic phase was dried over sodium sulphate, filtered and concentrated. Crystallization of the resulting brown oil from ethyl acetate/hexane gave 85 g of colourless γ-[(p-chlorophenyl)sulfonyl]tiglic aldehyde with m.p. 97°–99° C.

(c) A solution of 10.4 g of γ-[(p-chlorophenyl)-sulfonyl]tiglic aldehyde in 80 ml of methanol was treated with 8.68 g of methyl orthoformate and 80 mg of 85 percent phosphoric acid while gassing with nitrogen and stirred overnight at 30° C. Subsequently, the reaction mixture was poured into aqueous sodium hydrogen carbonate solution and extracted with methylene chloride. The organic phase was dried over sodium sulphate, filtered and concentrated. There was thus obtained quantitatively γ-[(p-choro-phenyl)sulfonyl]tiglic aldehyde dimethyl acetal which crystallized spontaneously (m.p. 60°–62° C.).

(d) 4.5 g of γ-[(p-chlorophenyl)sulfonyl]tiglic aldehyde dimethyl acetal were dissolved in 22 ml of tetrahydrofuran under an inert gas. The solution was cooled to −70° C. and treated dropwise firstly with 9.11 ml of a 1.6M solution of butyllithium in hexane and then within 20 minutes with a solution of 2.57 g of 12′-apo-β-caroten-12′-al in 30 ml of tetrahydrofuran. The reaction mixture was stirred at −70° C. overnight and then treated within 5 minutes with 5.6 ml of acetic anhydride. The mixture was stirred for 6 hours at about 3° C. (cooling with an ice bath), then treated with 26 ml of 28 percent aqueous sodium hydroxide solution and stirred at room temperature overnight. Thereafter, the organic phase was separated, diluted with diethyl ether, washed neutral with aqueous sodium hydrogen carbonate solution and with sodium chloride solution, dried over sodium sulphate, filtered and concentrated. There were thus obtained 8 g of crude (all-E)-4-[(p-chlorophenyl)sulfonyl]-2,6,11,15-tetramethyl-17-(2,2,6-trimethyl-1-cyclohexen-1-yl)-2,4,6,8,10,12,14,16-heptadecaoctaenal dimethyl acetal as a red oil.

(e) A mixture of 8 g of crude (all-E)-4-[(p-chlorophenyl)sulfonyl]-2,6,11,15-tetramethyl-17-(2,2,6-trimethyl-1-cyclohexen-1-yl)-2,4,6,8,10,12,14,16-heptadecaoctaenal dimethyl acetal, 30 ml of tetrahydrofuran, 30 ml of water, 3 ml of diethylamine and 6.5 g of sodium dithionite was stirred at room temperature for 2 hours. Subsequently, the reaction mixture was acidified with dilute sulphuric acid (hydrolysis of the acetal group), then poured into aqueous sodium hydrogen carbonate solution and diluted with diethyl ether. The organic phase was washed neutral, dried over sodium sulphate, filtered and concentrated. There were thus obtained 4.1 g of red, oily crude product of 8′-apo-β-caroten-8′-al. After heating to reflux with heptane (isomerization), column chromatography and crystallization from pentane there could be obtained pure product (all-E component 97%) with m.p. 126°–128° C.

EXAMPLE 10

(a) A solution of 7.6 g of γ-[(p-chlorophenyl)-sulfonyl]tiglic aldehyde dimethyl acetal in 100 ml of tetrahydrofuran was cooled to −70° C. and treated dropwise within 10 minutes with 15 ml of a 1.6M solution of butyllithium in hexane. The reaction mixture was then treated within 10 minutes with a solution of 1.78 g of (all-E)-2,7-dimethyl-2,4,6-octatrienedial in 50 ml of tetrahydrofuran and stirred at −70° C. overnight. Subsequently, the reaction mixture was treated dropwise at −70° C. with 15 ml of acetic anhydride and stirred with increasing temperature (up to −20° C.). After 4 hours the reaction mixture was treated dropwise at −20° C. with 66 ml of 28 percent sodium hydroxide solution and stirred overnight, whereby the temperature was allowed to rise to room temperature. Thereafter, the reaction mixture was poured into a mixture of ice and dilute aqueous sodium chloride solution and diluted with diethyl ether. The organic phase was dried over sodium sulphate, filtered and concentrated. There were thus obtained 10 g of crude (all-E)-4,13-bis-[(p-chlorophenyl)sulfonyl]-2,6,11,15-tetramethyl-2,4,6,8,10,12,14-hexadecaheptaenedial bis(dimethyl acetal) as a red oil.

(b) A mixture of 10 g of crude (all-E)-4,13-bis-[(p-chlorophenyl)sulfonyl]-2,6,11,15-tetramethyl-2,4,6,8,10,12,14-hexadecaheptaenedial bis(dimethyl acetal), 150 ml of tetrahydrofuran, 100 ml of water, 36 ml of diethylamine and 24 g of sodium dithionite was stirred at room temperature for 40 minutes and then treated with dilute sulphuric acid. The organic phase was diluted with diethyl ether, washed with aqueous sodium hydrogen carbonate solution, washed neutral with aqueous sodium chloride solution, dried over sodium sulphate, filtered and concentrated. There were thus obtained 4.8 g of a red oil as a crude product of crocetin dialdehyde. Filtration of the crude product through silica gel and crystallization from methylene chloride/methanol gave crystalline crocetin dialdehyde with m.p. 193°–195° C. and an all-E content of 98%. The above mother liquor (2.1 g) with a content of 78% crocetin dialdehyde was not worked-up.

We claim:
1. Compounds of the general formula

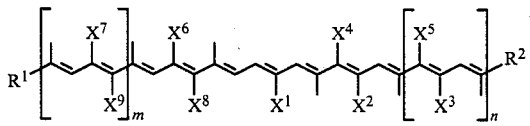

wherein m and n are independently 0 or 1, $R^1$ and $R^2$ are selected from the group consisting of 4-methyl-3-pentenyl, formyl protected with an acetal protecting group, carboxy, carboxy esterified with an ester protecting group, and a group of the formula:

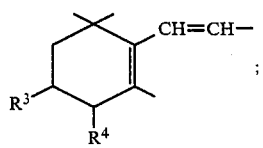

$R^3$ and $R^4$ are hydrogen, hydroxy, hydroxy protected with a protecting group, oxo or oxo protected with a protecting group; with the proviso that when m is 1, $R^1$ is 4-methyl-3-pentenyl; and when m is 0, $R^1$ is other than 4-methyl-3-pentenyl; and when n is 1, $R^2$ is 4-methyl-3-pentenyl and when n is 0, $R^2$ is other than 4-methyl-3-pentenyl; only one of $X^1$, $X^2$, $X^3$, $X^4$ and $X^5$ being a sulfonyl residue while the others are hydrogen; and $X^6$, $X^7$, $X^8$ and $X^9$ all being hydrogen except in the case where $R^1$ and $R^2$ are both selected from the same group and $X^1$ is hydrogen, then in this case, $X^6$ can be either hydrogen or a sulfonyl residue if $X^2$ is a sulfonyl residue, $X^7$ can be either hydrogen or a sulfonyl residue if $X^3$ is a sulfonyl residue, $X^8$ can be either hydrogen or a sulfonyl residue, if $X^4$ is a sulfonyl residue, and $X^9$ can be either hydrogen or a sulfonyl residue if $X^5$ is a sulfonyl residue.

2. The compound of claim 1 wherein one of $X^1$, $X^2$ or $X^3$ is a sulfonyl radical.

3. The compound of claim 2 wherein $X^2$ is a sulfonyl radical, $X^6$ is hydrogen or a sulfonyl radical and $X^1$, $X^3$, $X^4$, $X^5$, $X^7$, $X^8$ and $X^9$ are hydrogen.

4. The compound of claim 3 wherein both $X^2$ and $X^6$ are a sulfonyl radical and $R^1$ and $R^2$ are both selected from the same group.

5. The compound of claim 3 wherein the compound is in the all E-form.

6. The compound of claim 5 wherein said compound is (all E)-β,β-caroten-11,11'-ylene-bis[(p-chlorophenyl)sulfone].

7. The compound of claim 5 wherein said compound is (all-E)-R,R'-zeaxanthin-11,11'-ylene-bis[(p-chlorophenyl)sulfone diacetate.

8. The compound of claim 5 wherein said compound is 4,4',4'-bis(ethylenedioxy)-canthaxanthin-11,11'-ylene bis-[(p-chlorophenyl)sulfone].

9. The compound of claim 2 wherein $X^1$ is a sulfonyl radical.

10. The compound of claim 9 wherein $R^1$ and $R^2$ are both selected from the same group.

11. The compound of claim 10 wherein said compound is in the all-E form.

12. The compound of claim 11 wherein said compound is (all-E)-β,β-caroten-15-yl(p-chlorophenyl)sulfone) or (all-E)-β,β-caroten-15-yl phenylsulfone.

13. The compound of claim 2 wherein $X^3$ is a sulfonyl residue.

14. The compound of claim 13 wherein m and n is 1 and $R^2$ is 4-methyl-3-pentenyl.

15. The compound of claim 14 wherein $R^1$ is 4-methyl-3-pentenyl.

16. The compound of claim 15 wherein said compound is (all-E)-lycopen-7,7'-ylene bis-[p-chlorophenyl)sulfone].

17. The compound of claim 3 wherein m and n are 0 and $R^1$ is selected from a different group than $R^2$.

18. The compound of claim 17 wherein $R^1$ is an acetalized formyl.

19. The compound of claim 18 wherein said compound is (all-E)-4-[(p-chlorophenyl)sulfonyl]-2,6,11,15-tetramethyl-17-(2,2,6-trimethyl-1-cyclohexen-1-yl)-2,4,6,8,10,12,14,16-heptadecaoctaenal dimethyl acetal.

20. The compound of claim 4 wherein said compound is (all-E)-4,13-bis[(p-chlorophenyl)sulfonyl]-2,6,11,15-tetramethyl-2,4,6,7,10,12,14-hexadecaheptaenedial bis(dimethyl acetal).

21. The compound of claim 5 wherein said compound is (all E)-β, β-carotene-11,11'-ylene-bis[phenylsulfone].

22. The compound of claim 5 wherein said compound is (all-E)-R, R'-zeaxanthin-11,11'-ylene-bis[phenylsulfone].

* * * * *